(12) United States Patent
Nakahara et al.

(10) Patent No.: US 7,319,167 B2
(45) Date of Patent: Jan. 15, 2008

(54) METHOD FOR DISTILLING (METH)ACRYLIC ACID AND/OR THE ESTER THEREOF

(75) Inventors: Sei Nakahara, Himeji (JP); Kazuhiko Sakamoto, Kobe (JP); Yukihiro Matsumoto, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 478 days.

(21) Appl. No.: 10/840,252

(22) Filed: May 7, 2004

(65) Prior Publication Data

US 2004/0230074 A1   Nov. 18, 2004

(30) Foreign Application Priority Data

May 9, 2003 (JP) .............................. 2003-131509

(51) Int. Cl.
*C07C 51/42* (2006.01)
(52) U.S. Cl. .................................... 562/600
(58) Field of Classification Search ............... 560/218; 562/600
See application file for complete search history.

(56) References Cited

U.S. PATENT DOCUMENTS

| | | | |
|---|---|---|---|
| 4,369,077 A | 1/1983 | Saito | |
| 5,371,280 A | 12/1994 | Haramaki et al. | |
| 6,458,989 B1* | 10/2002 | Aichinger et al. | 560/218 |
| 6,506,930 B1 | 1/2003 | Venter et al. | |
| 6,599,397 B2 | 7/2003 | Sakamoto et al. | |
| 6,613,196 B2 | 9/2003 | Hamamoto et al. | |
| 2002/0008010 A1* | 1/2002 | Hamamoto et al. | 203/8 |

FOREIGN PATENT DOCUMENTS

| | | |
|---|---|---|
| GB | 1 402 002 | 8/1975 |
| JP | 57-42302 | 3/1982 |
| JP | 5-51403 | 3/1993 |
| JP | 7-072204 | 3/1995 |
| JP | 11-236352 | 8/1999 |
| JP | 2001-348360 | 12/2001 |
| JP | 2002-035575 | 2/2002 |
| JP | 2003-113138 | 4/2003 |
| WO | 99/50221 | 10/1999 |

OTHER PUBLICATIONS

Perry's Chemical Engineer's Handbook 4th ed. (1963) p. 13-2.*

* cited by examiner

*Primary Examiner*—Karl Puttlitz
(74) *Attorney, Agent, or Firm*—Wenderoth, Lind & Ponack, L.L.P.

(57) ABSTRACT

A method for distilling (meth)acrylic acid and/or the ester thereof by withdrawing vapor generated in a distillation column by distillation from the top of the column, condensing the vapor to give a condensate, and circulating part of the condensate as reflux liquid into the distillation column from the top thereof, comprising the step of adding a polymerization inhibitor to said condensate and said reflux liquid. This method enables maintaining the purity and quality of (meth)acrylic acid and/or the ester thereof at a certain level or higher, suppressing generation of polymers in the rectification column and suppressing polymerization of the condensate obtained by distillation in the incident facilities of the column such as condenser, condensate tank, and the like. In addition, the method enables reduction in the amount of polymerization inhibitor used while suppressing polymerization in the intermediate distillation columns (except the final rectification column).

14 Claims, 2 Drawing Sheets

METHOD FOR DISTILLING (METH)ACRYLIC ACID AND/OR THE ESTER THEREOF

BACKGROUND OF THE INVENTION

1. Field of the Invention

The present invention relates to a method for preventing polymerization of (meth)acrylic acid and/or the ester thereof during production thereof, and in particular to a method for effectively preventing generation of polymers, which often causes problems during distillation of liquids containing (meth)acrylic acid and/or the ester thereof.

2. Description of the Related Art (Meth)acrylic acid and the ester thereof have been hitherto produced by various processes. Acrylic acid is prepared, for example, by catalytically oxidizing propylene and/or acrolein (hereinafter, referred to as "propylene and the like") with a molecular oxygen-containing gas in gas phase, collecting an aqueous acrylic acid solution obtained by bringing the reaction products (reaction gas) obtained into contact with an absorption liquid, and then distilling the aqueous acrylic acid solution. For production of high-purity acrylic acid suitable as an industrial product, it is desirable to remove impurities contained in the aqueous acrylic acid solution, such as formaldehyde, furfural, benzaldehyde, propionic acid, formic acid, acetic acid, maleic acid, and the like as much as possible by distillation or other methods, but because the relative volatility of acrylic acid to water or acrylic acid to acetic acid is small, it is difficult to obtain high-purity acrylic acid in a simple distillation process, and thus these impurities were removed by various distillation methods combined. For example, such an aqueous acrylic acid solution is first distilled together with an azeotropic solvent (azeotropic distillation) to remove water and low-boiling components, giving an acrylic acid-containing solution containing high-boiling impurities and polymerization inhibitors, and then the high-boiling impurities and polymerization inhibitors are removed from the acrylic acid-containing solution by various other distillation methods. In addition, additional distillation, crystallization or the like is conducted as needed for removal of the trace amounts of impurities and production of high-purity acrylic acid.

In the distillation process, the vapor generated by distillation is withdrawn from the top of the distillation column and condensed, and part of the condensate is circulated as the reflux liquid into the distillation column from the top thereof. As many polymers are generated in incidental facilities of the column such as the condenser, condensate tank, and the like, it is required to suppress generation of polymers in these incidental facilities of column for more stabilized operation thereof. In addition, it is needed to maintain the concentration of polymerization inhibitors added into the distillation column at a certain level or higher for securing the potential of the polymerization inhibitors, and hence to add the polymerization inhibitors continuously into the distillation column, as the polymerization inhibitors are also distilled off continuously from the distillation column.

Various methods, for example, of raising the concentration of polymerization inhibitors in the distilling solution (feed solution) and of directly supplying the polymerization inhibitor into the distillation column, are adopted to solve the problems above (e.g., Japanese. Examined Patent Publication No. Hei7-72204 and Japanese unexamined patent application No. Hei11-236352). However, even though capable of suppressing polymerization in the distillation column, these methods cannot suppress generation of polymers in the condenser if the polymerization inhibitors are removed from the bottom of the column. Accordingly, a polymerization inhibitor is added to the condensate for raising the concentration of polymerization inhibitor in the condensate and thus for preventing generation of polymers in the incidental facilities of column, and the condensate is circulated into the distillation column for preventing polymerization in the distillation column (e.g., Japanese unexamined patent application No. 2001-348360).

However, if the polymerization inhibitor is added to the condensate in the amount sufficient for preventing polymerization in the distillation column, the concentration of the polymerization inhibitor in the condensate becomes higher than the amount required, and thus such methods also raised the problem of additional cost, for example, for installing an additional distillation process for removal of the polymerization inhibitor.

For example, in the case of a high-boiling impurity separation column, which has a relatively high distillation temperature, the concentration of polymerization inhibitor should be raised to a relatively high level for effective prevention of polymerization in the distillation column and the concentration of polymerization inhibitor in the condensate should also be raised. However, because such polymerization inhibitors should be removed before the final purified product is obtained, such increase in the concentration of polymerization inhibitors in the condensate caused the problem that it demands an additional distillation process, or expansion of the distillation column facility for removal of the polymerization inhibitors.

Alternatively, in the case of rectification column in the final distillation process, if a polymerization inhibitor higher in polymerization-inhibiting potential, which exerts a greater effect even with a small amount thereof, such as phenothiazine or an N-oxyl compound, is added to condensate and part of the condensate is circulated into the column for prevention of polymerization in the distillation column, the incidental facilities of column and of the condensate for the purpose of maintaining the purity of the condensate obtained by distillation, the purified product from such a process may have a purity satisfying the requirements for the product, but the use of such a polymerization inhibitor causes the problem of inferior quality due to coloring of acrylic acid, as phenothiazine or the N-oxyl compound is a colored polymerization inhibitor. Although addition of a polymerization inhibitor less coloring, such as hydroquinone monomethylether or the like, is examined for prevention of decrease in quality due to coloring, such a polymerization inhibitor should be added in a greater amount due to its inherent low polymerization-inhibiting potential for prevention of polymerization in the column, and thus caused the problem of lower purity of the final purified product. In this manner, it was difficult to maintain the purity and quality of the purified product at a certain level or higher and simultaneously to suppress polymerization sufficiently in the distillation column during distillation in the final rectification column, and thus it was frequently required to discontinue operation of the distillation column and wash and remove the polymers generated in the distillation column.

The present invention has been accomplished taking into account the circumstances above, and an object of the invention is to provide a method for suppressing generation of polymers in a distillation column used in the distillation process of (meth)acrylic acid and/or (meth)acrylic ester, and suppressing polymerization of the condensate obtained by distillation in the incidental facilities of column such as condenser, condensate tank, and the like.

In particular, an object of the present invention is to provide a method for maintaining the purity and quality of (meth)acrylic acid and/or the ester thereof at a certain level or higher, suppressing generation of polymers in a distillation column, and suppressing polymerization of the condensate obtained by distillation in the incidental facilities of the column during distillation in the final rectification column.

SUMMARY OF THE INVENTION

The present invention that solved the above problems is a method for distilling (meth)acrylic acid and/or the ester thereof by withdrawing vapor generated in a distillation column by distillation from the top of the column, condensing the vapor to give a condensate, and circulating part of the condensate as reflux liquid into the distillation column from the top side thereof, comprising the step of adding a polymerization inhibitor to said condensate and said reflux liquid.

Another aspect of the present invention is a method for distilling (meth)acrylic acid and/or the ester thereof by withdrawing the vapor generated in a distillation column by distillation from the top of the column, condensing the vapor to give a condensate, circulating part of the condensate thus condensed as reflux liquid into the distillation column from top side thereof, and feeding the other part of said condensate as circulating liquid into the lines connecting the condenser and/or the distillation column and said condenser, comprising the steps of adding a polymerization inhibitor to said condensate and/or said circulating liquid, and adding a polymerization inhibitor to reflux liquid.

In practicing the present invention, it is preferably to circulate part of the reflux liquid into the distillation column from the top side thereof, circulate the other part of the reflux liquid into the distillation column from a position lower than the top side thereof, and additionally add a polymerization inhibitor to the reflux liquid circulated from the lower position. It is also favorable that the polymerization inhibitor added to the reflux liquid, which is supplied to the line connected to the position lower than the top of the distillation column, is different from the polymerization inhibitor added to the reflux liquid circulated from the top side of the distillation column, the condensate, or the circulating liquid.

Further, in the present invention, the distillation column is preferably the rectification column for obtaining the final purified product.

These and other objects, features and advantages of the present invention will become more apparent upon reading of the following detailed description along with the accompanied drawings.

DETAILED DESCRIPTION OF THE PREFERRED EMBODIMENTS OF THE INVENTION

Figure 1:
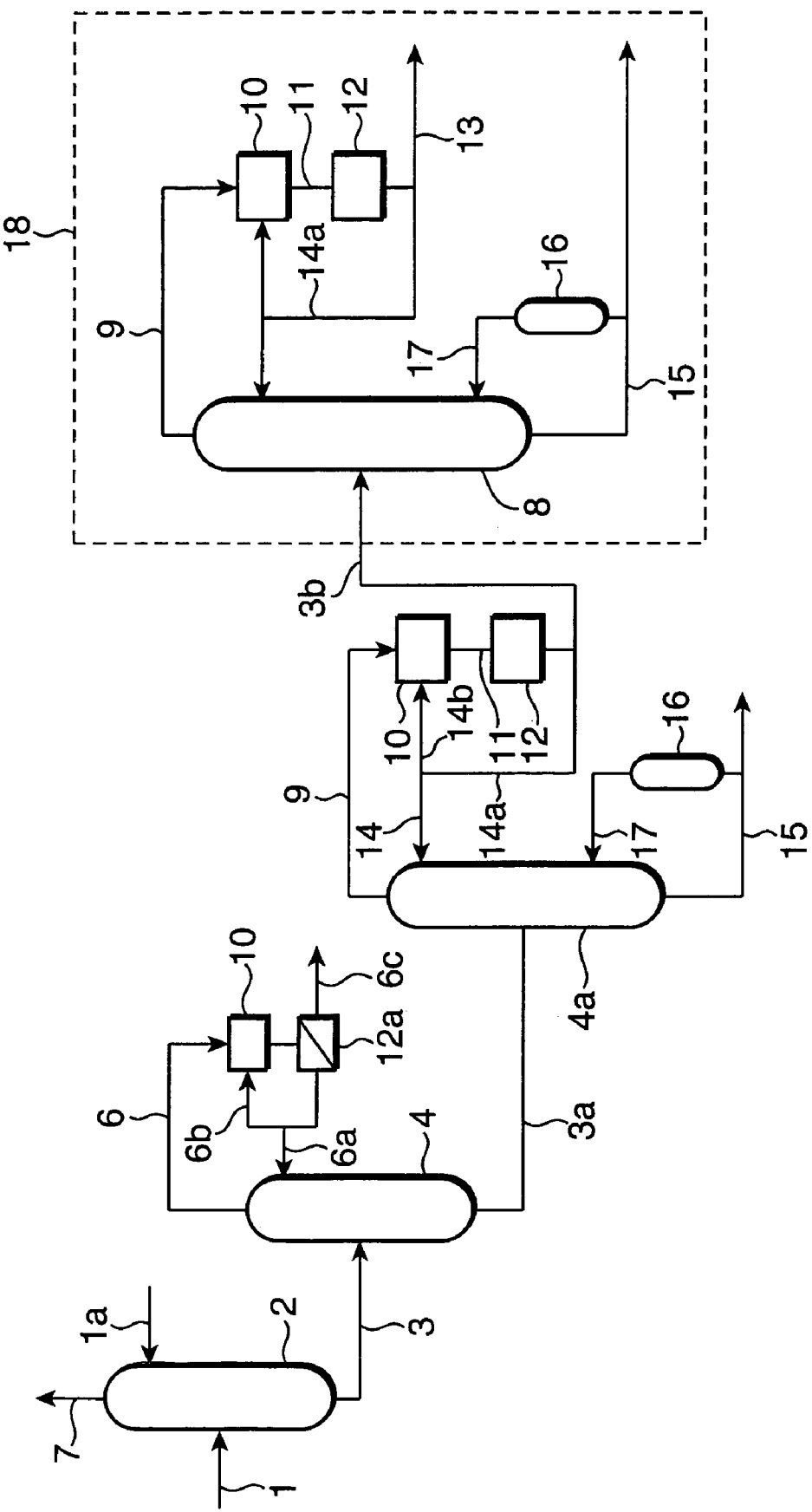
FIG. 1 is a schematic diagram of a process for producing acrylic acid.

After an intensive study to solve the problems above, the present inventors have found an effective method of suppressing generation of polymers in the distillation column and simultaneously suppressing polymerization of the condensate obtained by distillation in incidental facilities of the column such as the condenser and the like, as described below. In particular, the present inventors have found an effective method of preventing polymerization that allows suppression of the polymerization in the distillation column and the incident facilities thereof while maintaining the purity and quality of (meth)acrylic acid and/or the ester thereof obtained by condensation in the rectification column at a certain level or higher.

Hereinafter, the present invention will be described using the process of manufacturing acrylic acid as a typical example, but the method according to the present invention is not limited to the process of manufacturing acrylic acid, and may be also used in the processes for production of methacrylic acid, and (meth)acrylic ester such as methyl (meth)acrylate, ethyl (meth)acrylate, n-butyl (meth)acrylate, 2-ethylhexyl (meth)acrylate, 2-hydroxyethyl (meth)acrylate, 2-hydroxypropyl (meth)acrylate, cyclohexyl (meth)acrylate, t-butyl (meth)acrylate, i-nonyl (meth)acrylate, diethylaminoethyl (meth)acrylate, i-octyl (meth)acrylate, and the like.

As polymers are generated more frequently in absorption column and during transport of the distilling solution in the processes of manufacturing these (meth)acrylic acid and the ester thereof, the polymerization inhibitor described below may be added if desired. The polymerization inhibitor may be added to the distilling solution or into the absorption column and the transport lines directly.

The polymerization inhibitors are not particularly limited and examples thereof are polymerization inhibitors known in the art including: N-oxyl compounds such as 2,2,6,6-tetramethylpiperidinoxyl, 4-hydroxy-2,2,6,6-tetramethylpiperidinoxyl, 4,4',4"-tris-(2,2,6,6-tetramethylpiperidinoxyl) phosphite, and the like; phenol compounds such as hydroquinone, hydroquinone monomethylether, pyrogallol, catechol, resorcin, 2,4-dimethyl-6-t-butylphenol, and the like; phenothiazine compounds such as phenothiazine, bis-(a-methylbenzyl) phenothiazine, 3,7-dioctylphenothiazine, bis-(a-dimethylbenzyl)phenothiazine, and the like; copper dimethyldithiocarbamate, copper dibutyldithiocarbamate, and the like. The polymerization inhibitors may be used alone or in combination of 2 or more inhibitors.

The kinds of the polymerization inhibitors used in distillation columns other than rectification column (hereinafter, referred to as intermediate distillation columns as a whole), such as azeotropic distillation column, low-boiling impurity separation column, high-boiling impurity separation column, and the like, are also not particularly limited, and the polymerization inhibitors are preferably added according to the method of present invention described below. In addition, with respect to the final rectification column, it is recommended to select a polymerization inhibitor suitable for the method of the present invention described below and add the polymerization inhibitor according to the method of the present invention for maintaining the quality and purity of the purified product.

Hereinafter, the method of the present invention will be described with reference to FIG. 1, which illustrates an example of the process for manufacturing acrylic acid, and FIGS. 2 and 3, which show schematic diagrams of the rectification process 18 in the same process. As will be described below, the method of the present invention is characterized in that a polymerization inhibitor is added to the condensate and the reflux liquid, or that a polymerization inhibitor is added to the condensate and/or the circulating liquid, and at the same time to the reflux liquid circulated into the distillation column from the top side thereof. Therefore, the methods according to the present invention is not limited to the following manufacturing processes, and it should be understood that any modifications that do not interfere with the advantageous effects of the invention are also included in the scope of the present invention.

The products obtained from propylene and/or acrolein by catalytic oxidation are fed via a line 1 into an absorption column 2. The products generated by catalytic gas-phase oxidation of propylene and the like with a molecular oxygen-containing gas or the like under an arbitrary condition are usually provided as a reaction gas. An absorption liquid (e.g., water) was introduced via a line la into the absorption column 2, and brought into contact with the products in the absorption column 2. Acrylic acid contained in the products is absorbed in this manner to give an aqueous acrylic acid solution. The aqueous acrylic acid solution contains, in addition to acrylic acid, unreacted acrolein and byproducts (impurities) such as formaldehyde, furfural, benzaldehyde, propionic acid, formic acid, acetic acid, maleic acid, and the like. The aqueous acrylic acid solution is supplied into a distillation column (not shown in the figure) if desired to remove low-boiling products (impurities having a boiling temperature lower than that of acrylic acid) such as acrolein and others, and then fed via a line 3 into an azeotropic distillation column 4. In the azeotropic distillation column 4, low-boiling products such as water, acetic acid, and others are removed from the aqueous acrylic acid solution by azeotropic distillation using one or more publicly known azeotropic solvents fed therein such as toluene, xylene, hexane, heptane, cyclohexane, methylisobutylketone, butyl acetate, and the like. The low-boiling products and the azeotropic solvent(s) are removed via a line 6 from the top of the distillation column. Alternatively, acrylic acid, high-boiling impurities (impurities having a boiling temperature higher than that of acrylic acid) such as maleic acid, acrylic acid dimer, and the like, and polymerization inhibitors are withdrawn via a line 3a from the bottom of the column as an acrylic acid-containing solution. The vapor containing low-boiling products, azeotropic solvent(s) and the like withdrawn from the top of the column is condensed in a condenser 10, and fed into a solvent separator 12a. The azeotropic solvent is separated in the solvent separator 12a from a phase mainly containing water (aqueous phase), and circulated via a line 6a into the azeotropic distillation column 4, while the remaining aqueous phase is supplied to any process via a line 6c, but at least part thereof is preferably sent via the line la into the absorption column 2 and reused as the absorption liquid for absorption of acrylic acid. The acrylic acid-containing solution withdrawn via the line 3a from the bottom of the column is additionally sent if desired to a low-boiling product separation column (not shown in the figure) for removal of low-boiling products. After removal of particular impurities, the acrylic acid-containing solution is then introduced into a high-boiling impurity separation column 4a.

In the high-boiling impurity separation column 4a, the high-boiling impurities and the polymerization inhibitor(s) are removed as the bottom effluent from the bottom of the column by distillation, while crude acrylic acid is withdrawn from the top of the column (or from the side of the column). The crude acrylic acid contains, in addition to acrylic acid, polymerization inhibitors that are not removed by distillation (and polymerization inhibitors additionally added after distillation), trace amounts of impurities that are not completely removed by distillation, and others. The crude acrylic acid (vapor) withdrawn from the top of the column is condensed in a condenser 10, and part of condensate in the condensate tank 12 may be circulated into the distillation column. The crude acrylic acid withdrawn from the high-boiling impurity separation column 4a is then fed via a line 3b into a rectification column 8.

If present as impurities in the crude acrylic acid, low-boiling products are distilled together with acrylic acid from the top of the column, leading to decrease in the purity of acrylic acid, and thus if the crude acrylic acid contains a significant amount of low-boiling products, it is preferable to reduce the amount of low-boiling products to a desirable value by redistilling the crude acrylic acid before it is sent to the rectification column 8.

In the rectification column 8, an aldehyde-modifying agent, such as hydrazine, phenylhydrazine, or the like, may be previously added to the feed solution, or introduced directly into the column for reduction in the content of aldehydes in the acrylic acid.

The rectification column 8 according to the present invention is the final distillation column for production of high-purity acrylic acid. The high-purity acrylic acid can be obtained by removing the impurities by repeated distillations of the feed solution containing mainly the desired purification product, such as acrylic acid. In the present invention, the high-purity acrylic acid is an acrylic acid that has a purity satisfying the requirements as an industrial product, and more specifically having a purity of preferably 99.5% or more.

Specific "configurations" of the distillation columns used in the processes for production of acrylic acid the present invention, including azeotropic distillation column 4, high-boiling impurity separation column 4a, rectification column 8, and the like, may be selected according to the desirable applications, and thus are not particularly limited, and examples thereof include plate columns having any one of plates such as bubble cap tray, sieve tray, valve tray, and the like; and packed columns packed with any one of packing materials such as Raschig ring, Lessing ring, ball ring, and the like. In the present invention, plate columns fitted with sieve trays, which exhibit excellent performance in commercial scale distillation, are favorably used. In using the plate columns, the types of vapor-liquid contact are not particularly limited, and any types of contact, including crosscurrent, countercurrent, concurrent and others, may be employed. The number of plates to be placed in a column may be suitably selected according to the diameter and capacity of the column and the desirable conditions thereof such as the purity of product. Further, incident facilities of the distillation column are not particularly limited, and, for example, heating means such as reboiler, heater, heating jacket, and the like may be additionally installed as needed. Furthermore, the feed rate of the feed solution and the operational conditions such as the temperature and pressure in the distillation column and others are not particularly limited, and may be selected suitably according to the desired applications, and pressure-control and feed rate-control valves may be additionally installed arbitrarily.

In the present invention, the incidental facilities of columns are facilities additionally added to the distillation column, such as condenser 10, condensate tank 12 (or azeotropic solvent separator 12a), line 11 connecting condenser 10 and condensate tank 12, line 14, line 13 for withdrawal of purified acrylic acid, and the like.

Acrylic acid contained in the crude acrylic acid fed into the rectification column 8 is vaporized by distillation, and the vapor is withdrawn from the top of the column via a line 9 into a condenser 10, where it is condensed in the condenser 10 to give a condensate. Impurities including polymerization inhibitors and the like are withdrawn as the bottom effluent via a line 15 form the bottom of the column. Part of the bottom effluent is supplied to a reboiler 16, and circulated as part of the heat source for heating the rectification column 8, and the other part of the bottom effluent is supplied to any other processes.

In the condenser 10, the vapor may be condensed by direct contact of the vapor with a refrigerant for condensation, for example, in a showering contact condenser, or by indirect heat exchange between the vapor and a refrigerant, for example, by supplying the vapor into the tubes of a shell-and-tube condenser and the refrigerant into the shells surrounding the tubes. Other publicly known condensers, such as coil and spiral heat exchangers, may also be employed.

The condensate obtained by condensation in the condenser 10 is sent via a line 11 into a condensate tank 12 and stored therein. Part of the condensate in the condensate tank 12 is supplied as the reflux liquid into the rectification column 8 from the top side thereof, and used for vapor-liquid contact with the vapor generated therein. The other part of the condensate in the condensate tank 12 may be supplied as a circulating liquid to the condenser 10 and/or to the line 9, which connect the rectification column 8 and the condenser 10. The condensate in the condensate tank 12 may be supplied via a line 13 to any other processing and production processes, or to the process for preparation for shipment as the product.

As the condensate obtained by distillation in the rectification column 8 contains almost no polymerization inhibitors, polymers are more easily generated in the incidental facilities of column such as condenser 10, the condensate tank 12, and the like. In addition, if part of the condensate is supplied as the reflux liquid into the rectification column 8 from the top side thereof, polymers tend to be generated in the rectification column 8 if the reflux liquid does not contain any polymerization inhibitors.

Thus, the condensate may be added with a polymerization inhibitor in a concentration sufficient to prevent polymerization in the rectification column 8 and then part of the condensate circulated into the rectification column 8, but in such a case, the purity and quality of the acrylic acid obtained via the line 13 decreases, although it is possible to suppress polymerization in the condensate tank 12 and the rectification column 8. Namely, if a polymerization inhibitor highly effective by addition only of a small amount thereof, such as an N-oxyl compound-based polymerization inhibitor, phenothiazine, copper dibutyldithiocarbamate, or the like, is added to the condensate, the polymerization may be avoided in the rectification column 8 without reducing the purity of acrylic acid unnecessarily, but the addition of the polymerization inhibitor to the condensate is unfavorable because it causes coloring of the condensate (acrylic acid) obtained via the line 13, leading to deterioration in product quality. Although a polymerization inhibitor that does not color acrylic acid such as hydroquinone monomethylether or the like may be added to the condensate for prevention of polymerization and of deterioration in quality due to coloration, the inhibitor is generally weaker in polymerization-inhibiting potential than the polymerization inhibitors described above such as N-oxyl compounds and the like. For that reason, if the condensate added with hydroquinone monomethylether is circulated into the rectification column, the amount of the inhibitor added should be raised for effective prevention of polymerization of the reflux liquid in the rectification column 8, compared to the case when an N-oxyl compound is added. However, the increase in the amount of polymerization inhibitor added to the condensate stored in the condensate tank 12 is undesirable, as it leads to decrease in the purity of the acrylic acid obtained via the line 13.

Accordingly, for the purpose of maintaining high polymerization-inhibiting property in the distillation column, keeping the purity and quality of acrylic acid at a certain level or higher, and preventing polymerization of the condensate obtained by distillation in the incidental facilities of column such as the condenser 10, condensate tank 12, and the like, it is recommended not only to add the polymerization inhibitor to the condensate but also to the reflux and circulating liquids as described below.

If a polymerization inhibitor is added to the condensate and the amounts of the polymerization inhibitor added to the reflux liquid and the condensate are favorably adjusted to a concentration required for maintaining the product quality at a certain level and at the same time preventing polymerization of the condensate in the incident facilities such as the condensate tank 12, condenser 10, and the like, and further the polymerization inhibitor added to the reflux liquid, i.e., part of the condensate, is at a concentration required for preventing polymerization in the column. The addition of the polymerization inhibitor to the reflux liquid at such a concentration that is required for preventing polymerization in the rectification column 8 allows reduction in the amount of the polymerization inhibitor added to the condensate, consequently permitting suppression of decrease in the purity of acrylic acid and at the same time suppression of the generation of polymers in the incidental facilities of column such as the condenser 10, condensate tank 12, and the like and also in the rectification column 8.

Alternatively, if a polymerization inhibitor is added to the circulating liquid, i.e., the other part of the condensate, as the circulating liquid is distilled back to the condensate, the amount of the polymerization inhibitor added to the circulating liquid is favorably adjusted to a concentration required for maintaining the product quality and preventing polymerization in the incidental facilities of columns in the similar manner to above.

If the effluent vapor passing through the line 9 is cooled, the vapor condenses in the line 9, sometimes causing generation and adhesion of polymers therein, and therefore, for the purpose of preventing polymerization due to condensation in the line 9, heating means such as heating jacket, heater, and the like for keeping the vapor in over-heated state (at a temperature above the dew point) may be additionally installed if desired to the line 9, or the circulating liquid containing the polymerization inhibitor may be added at any point of the line 9.

In the similar manner to the case where a polymerization inhibitor is added to the condensate above, the amount of the polymerization inhibitor added to the line 9 is adjusted to a concentration required for maintaining the product quality and preventing polymerization of the condensate including the circulating liquid. In addition, an additional polymerization inhibitor may be added to the condensate if needed, when it is supplied via the line 13 to other processing and production processes or the preparative process for shipment as the product.

Independent of the method of adding the polymerization inhibitor into the condensate described above, a polymerization inhibitor may be added to the reflux liquid at an amount required for preventing polymerization in the rectification column 8 as described above.

Because the incidental facilities of columns such as the condensate tank 12 and others are relatively cooler compared to any positions inside the rectification column 8 and thus have a smaller possibility of generating polymers, a polymerization inhibitor having smaller polymerization-inhibiting potential than those used for prevention of polymerization in the rectification column 8 may be used as the polymerization inhibitor used for prevention of polymerization of the condensate in the incidental facilities of columns. Even at a smaller concentration, the polymerization inhibitor can prevent the polymerization of the condensate sufficiently in incidental facilities of columns and the like and thus allows prevention of polymerization while maintaining the purity and quality of the acrylic acid obtained via the line 13 at a certain level or higher.

Accordingly, for example, phenol-based polymerization inhibitors, such as hydroquinone monomethylether, hydroquinone, 2,4-dimethyl-6-t-butylphenol, and the like, that do not cause coloring of acrylic acid are preferably used as the polymerization inhibitors added to the condensate and the circulating liquid.

If the polymerization inhibitor contained in the condensate is a polymerization inhibitor having a low polymerization-inhibiting potential and the amount of the polymerization inhibitor added is sufficient for preventing polymerization of the condensate and the like (to an extent not decreasing the purity and quality of the acrylic acid) as described above, polymerization in the rectification column 8 may not be sufficiently controlled even if part of the condensate is used as it is as the reflux liquid. Thus, it is preferable to raise the concentration of polymerization inhibitor by adding the polymerization inhibitor to the reflux liquid.

A phenol-based polymerization inhibitor or a polymerization inhibitor having high polymerization-inhibiting property may be used as the polymerization inhibitors added to the reflux liquids of the intermediate distillation columns. It is preferable to use the polymerization inhibitor having high polymerization-inhibiting property in view of the fact the reflux liquid is heated at high temperature in the distillation column. Favorable examples of the polymerization inhibitors having high polymerization-inhibiting property is at least one selected from the group consisting of N-oxyl-based polymerization inhibitor, amine-containing polymerization inhibitor and metallic polymerization inhibitor. Specific examples of N-oxyl-based polymerization inhibitor are 4-hydroxy-2,2,6,6-tetramethylpiperidinoxyl and the like. Examples of amine-type polymerization inhibitors include phenothiazine, phenylenediamine, and the like. A specific examples of metallic polymerization inhibitors are copper dibutyldithiocarbamate, manganese acetate, and the like. As the polymerization inhibitors added to the reflux liquids of the intermediate distillation columns are eventually removed in the rectification column 8, the kinds and amounts of the polymerization inhibitors added are not particularly limited. Favorably, the amount of the polymerization inhibitor is 1 to 1000 ppm with respect to the acrylic acid.

In contrast, polymerization inhibitors similar to those added to the condensate and the circulating liquid are preferred used as the polymerization inhibitor added to the reflux liquid of the rectification column 8. If the reflux liquid is supplied into the distillation column from the utmost top thereof (e.g., a position higher than the highest tray in the case of a plate column), the polymerization inhibitor added to the reflux liquid may be distilled back from the top of the column by entrainment, and thus use of the N-oxyl-based polymerization inhibitor, amine-type polymerization inhibitor, or metallic polymerization inhibitor described above may result in the contamination (e.g., coloring) of acrylic acid and affect the polymerization property of the resulting acrylic acid. Even if a polymerization inhibitor such as an N-oxyl compound or the like is used or the concentration of polymerization inhibitor in the reflux liquid is raised, it is possible to prevent effectively decrease in the purity and quality of acrylic acid due to the entrainment of polymerization inhibitors, by supplying part of the reflux liquid into the distillation column from the top thereof and the other part of the reflux liquid separately from a position lower than the top of the distillation column as set forth in FIG. 3, and further by adding a polymerization inhibitor to the reflux liquid supplied from the lower position for increase in the concentration of polymerization inhibitor. The specific supplying position may be decided arbitrarily, taking into account the amount of entrainment and the like.

The polymerization inhibitor to be added to the circulating liquid and/or the condensate may be adjusted to an amount sufficiently suppressing the generation of polymers of the condensate or in the incidental facilities of columns, and if hydroquinone monomethylether is added to the circulating liquid as the polymerization inhibitor for example, the polymerization inhibitor may be adjusted to a concentration of about 10 to 200 ppm with respect to the acrylic acid in the condensate. Addition thereof in such a range achieves the object of the invention, i.e., of preventing polymerization in the column while maintaining the purity of the acrylic acid in the condensate or the incidental facilities of column.

Alternatively, if hydroquinone monomethylether is added to the reflux liquid during the distillation of acrylic acid, the amount of hydroquinone monomethylether added to the reflux liquid is preferably adjusted to a concentration of about 100 to 5000 ppm with respect to the acrylic acid in the column for preventing polymerization in the rectification column 8. If the concentration of hydroquinone monomethylether in the condensate increases by entrainment, it is preferable to supply part of the reflux liquid into the rectification column 8 from a position lower than the top thereof as set forth in FIG. 3, and add a polymerization inhibitor to the reflux liquid supplied from the lower position in an amount adjusted to make the concentration of hydroquinone monomethylether in the column at about 100 to 5000 ppm with respect to acrylic acid.

In particular, if a polymerization inhibitor (having high polymerization-inhibiting property such as an N-oxyl compound or the like) different from the polymerization inhibitor added to the condensate is added to the reflux liquid, it is preferable to add the polymerization inhibitor to reflux liquid to be supplied from a position lower than the top position of the rectification column 8, from which part of the reflux liquid is supplied in the similar manner to above, in an amount adjusted to make the concentration thereof in the column at about 1 to 1000 ppm with respect to the acrylic acid, for the purpose of preventing contamination of polymerization inhibitors into the effluent above and polymerization in the distillation column.

In this manner, adjustment of the concentrations of polymerization inhibitors by controlling the methods of supplying polymerization inhibitors to the reflux liquid, condensate, and circulating liquid and the amounts thereof added respectively enables suppression of excessive decrease in the purity and quality of the purified acrylic acid obtained via the line 13, and also of polymerization in the rectification column 8 and incidental facilities of the column.

Figure 2:
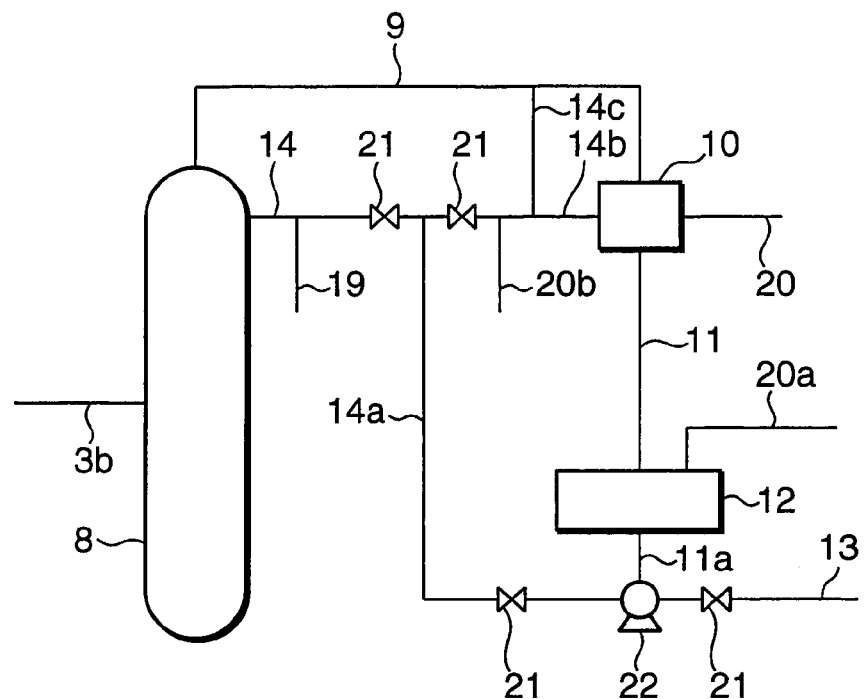
FIG. 2 is a schematic diagram illustrating the rectification process 18 as set forth in FIG. 1.
Figure 3:
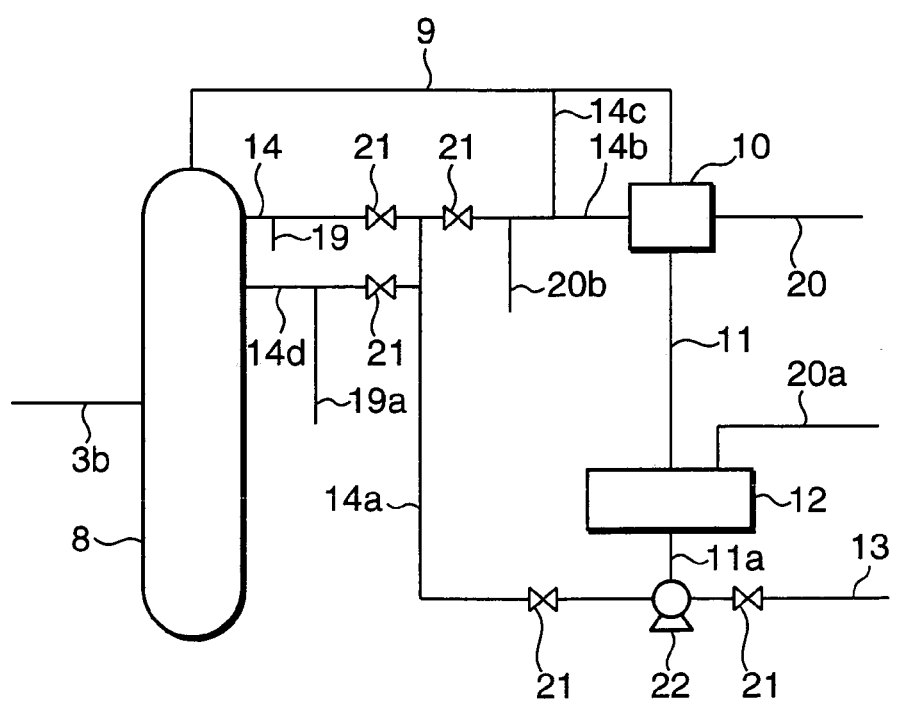
FIG. 3 is another schematic diagram illustrating the rectification process 18 as set forth in FIG. 1.

FIGS. 2 and 3 are schematic diagrams illustrating examples of the method of adding the polymerization inhibitor in the rectification process 18 shown in FIG. 1.

If a polymerization inhibitor is added to the condensate, the position of adding the polymerization inhibitor is not particularly limited and, for example, the inhibitor may be added directly to the condenser 10 (via line 20), and/or directly to the condensate tank 12 (via line 20a), and/or to any position in a line 11 (not shown in the figure), and/or to any position in the line 9 (via line 14C), as set forth in FIG. 2. The polymerization inhibitor may be of course added from any multiple positions to the condensate. As polymers are often found particularly in the line 9 connecting between the rectification column 8 and the condenser 10 and in the condenser 10, and also polymers derived from the condensate obtained in the condenser in the line 11 and the condensate tank 12, it is preferable to supply the circulating liquid added with a polymerization inhibitor to any point in the line 9 via the line 14c and at the same time into the condenser 10 via the line 14b, for effective prevention of polymerization. The position of supplying the polymerization inhibitor to the circulating liquid is not particularly limited, and thus the polymerization inhibitor may be added from any point, and for example, after installing a line 20b at any position in the line 14b, the polymerization inhibitor may be added via the line 20b as set forth in the figure.

In FIGS. 2 and 3, the reflux and circulating liquids are withdrawn from the condensate in condensate tank 12 via the same line 11a, and the circulating liquid is supplied via the lines 14a, 14b, and 14c to the condenser 10 and to the line 9, while the reflux liquid via the lines 14a, and 14 to the rectification column 8. However, the reflux and circulating liquids may be supplied respectively via independent lines connected to the condensate tank 12, and in addition, any other modifications are also possible. The configuration wherein these liquids are withdrawn via the same line 11a as shown in the figure is favorable, as it allows supply of these liquids only by a single supply pump and hence simplification of the facility.

It is recommended to add a polymerization inhibitor to the reflux liquid supplied via the line 14 into the rectification column 8, via a line 19 additionally installed for addition of the polymerization inhibitor at any point of the line 14. As the reflux liquid is part of the condensate, it certainly contains the polymerization inhibitor previously added to the condensate (hereinafter, the polymerization inhibitor added to the condensate is referred to as the "polymerization inhibitor A"; and the polymerization inhibitor added to the reflux liquid, the "polymerization inhibitor B"). The polymerization inhibitors A and B, may be the same polymerization inhibitor or different polymerization inhibitors.

In the present invention, the reflux liquid containing polymerization inhibitors A and B is fed via the line 14 into the rectification column 8. All of the reflux liquid may be fed into rectification column 8 from the ultimate top thereof (a position higher than the highest tray in the case of a plate column). Alternatively, the reflux liquid may be fed from any lower positions of the column via multiple lines as set forth in FIG. 3.

When the polymerization inhibitors A and B are different, for suppressing the contamination of the effluent vapor containing the polymerization inhibitor B by entrainment and raising the polymerization-inhibiting potential in the column, it is preferable to supply the reflux liquid containing the polymerization inhibitor A via the line 14 into the distillation column from the utmost top thereof and at the same time the reflux liquid added with polymerization inhibitor B via the line 19a and the line 14d connected to the rectification column 8 at a position lower than the utmost top thereof as set forth in FIG. 3. At the time, it is preferable to add polymerization inhibitor A via the line 19 for increasing the concentration of the polymerization inhibitor A in the reflux liquid fed via the line 14.

The connection position of the line 14d is preferably, for example in the case of a plate column, is a position 1 to 10 plates lower, and preferably 1 to 5 plates lower than the utmost top, for prevention of entrainment and polymerization in the column. Independent of whether the polymerization inhibitors A and B are the same or not, the polymerization inhibitors and the reflux liquid may be supplied from a plurality of positions. By controlling the supplying position and the kinds of polymerization inhibitors in this manner, it becomes possible to suppress the polymerization effectively at the ultimate top and inside the column, preventing such problems as decrease in the purity of acrylic acid due to contamination due to the vapor containing the polymerization inhibitor B and coloring of acrylic acid.

In addition, if the reflux liquid is fed separately (via lines 14 and 14d) as set forth in FIG. 3, it is recommended to supply the reflux liquid more via the line 14 than via line 14d from the viewpoint of keeping the distillation-separation efficiency higher, and more specifically, the ratio of the feed rates via line 14:line 14d is preferably in the range of 2:1 to 500:1.

If the polymerization inhibitor B is supplied directly into the rectification column 8 without being added to the reflux liquid, polymers are often generated in the feed line 14 (or additionally, in line 14d) for introducing the reflux liquid and at the portions thereof connected to the rectification column 8 (including portions supplying the reflux liquid, such as the spraying nozzle and outlet of the reflux liquid supplied, and the feed line extending inside the column, and the like), as the reflux liquid does not contain a sufficient amount of polymerization inhibitor. As the connection portions are heated to high temperature by the vapor in the column, the polymerization often occurs in the feed line and in the neighborhood of the inlet. For preventing these problems, it is desirable to raise the concentration of polymerization inhibitor in the reflux liquid sufficiently by adding the polymerization inhibitor B to the reflux liquid as described above and thus to prevent generation of polymers at the connecting portions.

It is undesirable to supply polymerization inhibitor directly into the rectification column 8, as it demands installation of additional a polymerization-inhibitor feed line and various control instruments. Therefore, it is preferable to dissolve the polymerization inhibitor in the condensate and the reflux liquid as described above, for effectively preventing polymerization in incidental facilities of columns and in the rectification column while keeping the quality of purified acrylic acid.

The polymerization inhibitor may also be fed directly into the intermediate distillation columns if desired from any positions of the columns or fed indirectly, for example, by dissolving the inhibitors in solvents such as the purified and crude acrylic acid, but the polymerization inhibitor is preferably supplied by dissolving it in the reflux liquid or the condensate, from the reasons similar to those for the above rectification column and from the easiness in handling the polymerization inhibitor.

The method of adding polymerization inhibitors according to the present invention as described above may be employed in intermediate distillation columns such as azeotropic distillation column, high-boiling impurity separation column, and the like, as well as in the rectification column. Application of the method of adding the polymerization inhibitor according to the present invention to other intermediate distillation columns allows more efficient prevention of polymerization in these columns and the incidental facilities thereof and reduction in the amount of polymerization inhibitor used, compared to the case where the polymerization inhibitor is added directly into the distillation columns.

For example, in the azeotropic distillation column 4 set forth in FIG. 1, vapor containing water, azeotropic solvents, low-boiling impurities (having a boiling point lower than that of acrylic acid) and a trace amount of acrylic acid is withdrawn via a line 6 from the top of the column and condensed in a condenser 10. The condensate is then separated into solvent and aqueous phases in a solvent separator 12a. The solvent separated in the solvent separator 12a is supplied as the reflux liquid via a line 6a to the top of the azeotropic distillation column 4. At that time, a polymerization inhibitor is added for prevention of polymerization in the distillation column. In addition, part of the solvent and/or part of the aqueous phase separated are circulated as the circulating liquid via a line not shown in the figure to the line 6, and a polymerization inhibitor is added to the reflux liquid, the condensate (and/or effluent vapor) and/or the circulating liquid in the similar manner to above. However, as acrylic acid is contained in the condensate only in a trace amount, the polymerization may be prevented by the polymerization inhibitor carried by entrainment from the reflux liquid added with the polymerization inhibitor, without any addition of an additional polymerization inhibitor to the condensate. Use of the method of adding the polymerization inhibitor as described above allows effective suppression of generation of polymers in the distillation columns and the incident facilities thereof. It is of course possible to add a polymerization inhibitor into the azeotropic distillation column 4 from any point thereof as well as to add the polymerization inhibitor to the reflux liquid and the condensate. For prevention of entrainment, part of the reflux liquid may be supplied from the top of the column and other part thereof from a position lower than the top position, in a similar manner to the rectification column 8.

Hereinafter, the method of the present invention will be described in detail with reference to EXAMPLES, but it should be understood that the present invention is not limited to the following EXAMPLES.

EXAMPLE

Example 1

A reaction gas containing acrylic acid prepared by catalytic gas-phase oxidation using propylene as a starting material was introduced via a line 1 into an absorption column 2 set forth in FIG. 1 and at the same time, water is introduced into the same column 2 via a line la for absorption of acrylic acid. At that time, a polymerization inhibitor (hydroquinone) was added to the water supplied from the line la via a line not shown in the figure in an amount adjusted to give a concentration of the polymerization inhibitor at 100 ppm with respect to acrylic acid, for prevention of polymerization of acrylic acid in the absorption column. The aqueous acrylic acid solution thus obtained was introduced via a line 3 into an azeotropic distillation column 4, and distilled together with azeotropic solvents (toluene and methylisobutylketone) fed via a line 6a. The azeotropic solvents, water and acetic acid were distilled of f via a line 6 by azeotropic distillation, while an acrylic acid-containing solution containing acrylic acid, high-boiling impurities and polymerization inhibitors was obtained via a line 3a from the bottom of the column. At that time, polymerization inhibitors (hydroquinone and copper dibutyldithiocarbamate) were added via a line not shown in the figure to the azeotropic solvents supplied via the line 6a, and the concentrations of the polymerization inhibitors were adjusted respectively to 200 ppm (hydroquinone) and 50 ppm (copper dibutyldithiocarbamate) with respect to acrylic acid, for prevention of polymerization of acrylic acid in the azeotropic distillation column. Subsequently, the acrylic acid-containing solution was introduced via a line 3a into a high-boiling impurity separation column 4a (no shell sieve tray: 30 plates), and distilled therein (operational pressure: 40 hpa; reflux ratio: 0.5; and distillate/feed rate: 0.9). High-boiling impurities and polymerization inhibitors were removed from the bottom of the column by distillation in the high-boiling impurity separation column 4a, while the vapor of crude acrylic acid, which contains no high-boiling impurities, is withdrawn from the top of the column and condensed in a condenser 10 to give crude acrylic acid. At that time, a polymerization inhibitor, hydroquinone monomethylether, was added to the condenser via a line not shown in the figure for prevention of polymerization of acrylic acid in the condensate. The amount of the polymerization inhibitor added was adjusted to 200 ppm with respect to acrylic acid. Part of the condensate was circulated as reflux liquid into the distillation column, and a polymerization inhibitor (hydroquinone monoethylether) was added to the reflux liquid in an amount adjusted to make the concentration thereof at 1,000 ppm with respect to acrylic acid in the distillation column.

After operation for 80 days, the high boiling point impurity separation column 4a and the condenser 10 were examined. There was completely no generation of polymers in the high boiling point impurity separation column 4a and almost no generation of polymers in the condenser 10. The crude acrylic acid obtained via the line 3b was colorless.

Example 2

The crude acrylic acid was distilled in a similar manner to EXAMPLE 1., except that copper dibutyldithiocarbamate was added replacing hydroquinone monomethylether as the polymerization inhibitor to the reflux in the high boiling point impurity separation column 4a at a concentration of 50 ppm with respect to the acrylic acid.

After operation for 80 days, the high boiling point impurity separation column 4a and the condenser 10 were examined. There was completely no generation of polymers in the high boiling point impurity separation column 4a and almost no generation of polymers in the condenser 10. The crude acrylic acid obtained was contaminated with copper dibutyldithiocarbamate at a concentration of 0.3 ppm and was slightly yellowish, which was negligible in terms of product quality.

Comparative Example 1

The crude acrylic acid was distilled in a similar manner to EXAMPLE 1., except that no polymerization inhibitor was added to the reflux fluid in the high boiling point impurity separation column 4a.

After operation for 30 days, there was observed an increase in pressure loss in the high boiling point impurity separation column 4a. After discontinuation of operation, examination of the high boiling point impurity separation column 4a and the condenser 10 revealed that there were no polymers observed in the condenser 10 but there were a great amount of polymers on the trays of the high boiling point impurity separation column 4a. The crude acrylic acid obtained via the line 3b was colorless.

Example 3

The crude acrylic acid obtained in EXAMPLE 2 was further distilled for production of purified acrylic acid. The crude acrylic acid was fed via a line 3b shown in FIG. 1 into rectification column 8 (no shell sieve tray having 20 stages) and distilled therein (operational pressure: 50 hpa; reflux ratio: 1.0; and distillate/feed rate: 0.95). The vapor of the acrylic acid generated by the distillation was fed from the top of the column via a line 9 into a condenser 10 and the resulting condensate was collected in a condensate tank 12. The effluent vapor was high purity acrylic acid (having a purity of 99.5% or more) containing no high boiling point impurities or polymerization inhibitors. Part of the condensate in the condensate tank 12 was supplied into the condenser 10 as set forth in FIG. 2, by spraying as the circulating liquid via a line 14b into the condenser 10 and bringing the circulating liquid into vapor-liquid contact with the vapor therein. At that time, a polymerization inhibitor (hydroquinone monomethylether) was added via a line 20b to the circulating liquid, and the concentration of the inhibitor was adjusted to 50 ppm with respect to the acrylic acid in the circulating liquid. In addition, part of the condensate in the condensate tank 12 was fed as the reflux liquid via a line 14 into the rectification column 8 from the top portion thereof. At that time, a polymerization inhibitor (hydroquinone monomethylether) was added via a line 19 to the reflux liquid, and the concentration of the inhibitor was adjusted to 500 ppm with respect to the acrylic acid in the column.

After operation for 100 days, examination of the rectification column 8 and the condenser 10 revealed that there are no observable polymers. In addition, there were no observable polymers in the lines 11, 14a, 14, and 14b and in the condensate tank 12 as well. The purified acrylic acid obtained via the line 13 was colorless and had a high purity (purity of 99.5% or more).

Comparative Example 2

Purified acrylic acid was prepared in the similar manner to EXAMPLE 3, except that no polymerization inhibitor (hydroquinone monomethylether) was added to the reflux liquid via the line 19 in the rectification column 8.

After operation for 10 days, the purified acrylic acid obtained via the line 13 was colorless and had a high purity (purity of 99.5% or more), but there was observed an increase of the pressure drop in the distillation column. Examination of the interior of the column by interrupting operation thereof revealed that there were a great amount of polymers inside the rectification column 8 although there were few in the condenser 10.

Comparative Example 3

Purified acrylic acid was prepared in the similar manner to EXAMPLE 3, except that phenothiazine was added replacing hydroquinone monomethylether to the reflux liquid via the line 19 in the rectification column 8 at a concentration of 100 ppm with respect to the acrylic acid in the column.

After operation for 100 days, the rectification column 8 and the condenser 10 were examined, but there were no observable polymers all therein. In addition, there were no polymers at all in the lines 11, 14a, 14, and 14b and in the condensate tank 12 as well. The purified acrylic acid obtained via the line 13 was colorless and had a high purity (purity of 99.5% or more), but was not suitable as purified acrylic acid, as it contained phenothiazine at a concentration of 1.3 ppm.

Example 4

In the rectification column 8, addition of the polymerization inhibitor (hydroquinone monomethylether) to the reflux liquid via the line 19 was terminated and ½₀ of the reflux liquid was supplied via a line 14d to the fifth tray from the top of the column as set forth in FIG. 3. Purified acrylic acid was prepared in a similar manner to EXAMPLE 3, except that phenothiazine was added via a line 19a in an amount of 100 ppm with respect to the acrylic acid in the column.

After operation for 100 days, the rectification column 8 and the condenser 10 were examined but there were no polymers observable at all therein. The purified acrylic acid obtained via the line 13 was colorless and had a high purity (purity of 99.5%). In addition, phenothiazine was not detected in the purified acrylic acid, and there were no generation of observable polymers in the lines 11, 11a, 14a, 14b, 14, and 14d and in the condensate tank 12 as well. In this way, supplying the reflux liquid via the 14 and 14d enables to effectively inhibit polymerization in rectification column.

Example 5

Acrylic acid and 2-ethylhexanol were placed in a reactor (not shown in the figure), and were subjected to an esterification reaction in the presence of a polymerization inhibitor (phenothiazine), using a strongly acidic ion-exchange resin as catalyst and removing the generated water. The mixture thus obtained from the esterification reaction was introduced into a low-boiling product separation column (not shown in the figure), and unreacted acrylic acid, 2-ethylhexanol and the low-boiling impurities generated by the reaction were removed from the top of the column, while crude 2-ethylhexyl acrylate containing high-boiling impurities and the polymerization inhibitor was obtained from the bottom of the column. The vapor withdrawn from the top of the column was condensed in a condenser, and part of the resulting condensate was supplied as the reflux liquid into the low-boiling product separation column from the top thereof and the other part of the condensate was supplied to other processes (not shown in the figure). At that time, the reflux liquid was supplied after it was added with a polymerization inhibitor (phenothiazine) for prevention of polymerization in the low-boiling product separation column. The crude 2-ethylhexyl acrylate was introduced into the rectification column 8 (no shell sieve tray: 30 plates) as set forth in FIG. 2 and distilled (operational pressure: 40 hpa; reflux ratio: 0.8; and distillate/feed rate: 0.95). The vapor of 2-ethylhexyl acrylate generated by distillation was fed via the line 9 into the condenser 10 and condensed therein. The condensate was stored in the condensate tank 12. The effluent vapor was high-purity 2-ethylhexyl acrylate (having a purity of 99.7% or more) not containing high-boiling impurities or polymerization inhibitors. A polymerization inhibitor (hydroquinone monomethylether) was added to the condensate in the condensate tank 12 via a line 20a, and the concentration of the polymerization inhibitor was adjusted to 10 ppm with respect to 2-ethylhexyl acrylate. Part of the condensate in the condensate tank 12 was supplied by spraying via a line 14c into the line 9 and via a line 14b into the condenser 10. In addition, other part of the condensate in the condensate tank 12 was supplied as the reflux liquid via the line 14 into the rectification column from the top thereof. At that time, a polymerization inhibitor (hydroquinone monomethylether) was supplied via the line 19 to the reflux liquid, and the concentration the polymerization inhibitor was adjusted to 200 ppm with respect to 2-ethylhexyl acrylate in the column.

After operation for 100 days, the distillation column and the condenser were examined, but there were no observable polymers at all therein. In addition, there was no generation of polymers at all in the lines 11, 14a, 14c, and 14 and in the condensate tank 12. The purified 2-ethylhexyl acrylate was colorless and had a high purity (purity of 99.7% or more).

Comparative Example 4

The 2-ethylhexyl acrylate solution was distilled in a similar manner to EXAMPLE 5, except that hydroquinone monomethylether was not added to the reflux liquid via line 19 in the rectification column 8.

After operation for 20 days, the purified 2-ethylhexyl acrylate obtained was colorless and had a high purity (purity of 99.7% or more), but the pressure drop in the distillation column increased. After interruption of distillation, the interior of the distillation column was examined and there were observed a great amount of polymers in the rectification column 8 although there were few in the condenser 10.

Comparative Example 5

The 2-ethylhexyl acrylate solution was distilled in a similar manner to EXAMPLE 5, except that no polymerization inhibitor (hydroquinone monomethylether) was added to the condensate in the condensate tank via the line 20a in the rectification column 8.

After operation for 30 days, the purified 2-ethylhexyl acrylate obtained was colorless, but there were polymers observable in the condensate. After interruption of distillation, the interior of the distillation column was examined and there were no polymers observable in the rectification column 8 but there was generation of polymers in the condenser 10 and in the condensate tank 12.

Comparative Example 6

In the rectification column 8, the 2-ethylhexyl acrylate solution was distilled in a similar manner to EXAMPLE 5, except that copper dibutyldithiocarbamate was added replacing hydroquinone monomethylether to the reflux liquid via the line 19 in an amount of 10 ppm with respect to the 2-ethylhexyl acrylate in the column. The purified 2-ethylhexyl acrylate obtained via the line 13 had a high purity (purity of 99.7% or more), but contained copper dibutyldithiocarbamate at a concentration of 0.5 ppm, and thus was yellowish in color and unsuitable as purified 2-ethylhexyl acrylate (inferior quality).

Example 6

In the rectification column 8, the 2-ethylhexyl acrylate solution was distilled in a similar manner to EXAMPLE 5, except that the addition of polymerization inhibitor (hydroquinone monomethylether) to the reflux liquid via the line 19 was terminated; 1/30 of the reflux liquid was supplied via the line 14d to the 7th trays from the top of the column as set forth in FIG. 3; a polymerization inhibitor (copper dibutyldithiocarbamate) was supplied via a line 19a to the reflux liquid in the line 14d; and the concentration of copper dibutyldithiocarbamate is adjusted to 10 ppm with respect to the 2-ethylhexyl acrylate in the column.

After operation for 100 days, the rectification column 8 and the condenser 10 were examined but there were no observable polymers at all. In addition, there were no polymers generated in the lines 11, 11a, 14a, 13, 14, and 14d or in the condensate tank 12. The purified 2-ethylhexyl acrylate obtained via the line 13 was colorless and had a high purity (purity of 99.7% or more). Further, no copper dibutyldithiocarbamate was detected in the purified 2-ethylhexyl acrylate.

This application is based on Japanese Patent application No. 2003-131509 filed on May 9, 2003, the contents of which are hereby incorporated by reference.

Although the present invention has been fully described by way of example with reference to the accompanying drawings, it is to be understood that various changes and modification will be apparent to those skilled in the art. Therefore, unless otherwise such changes and modifications depart from the scope of the present invention hereinafter defined, they should be construed as being included therein.

What is claimed is:

1. A method for distilling (meth)acrylic acid and/or the ester thereof by withdrawing vapor generated in a distillation column by distillation from the top of the column, condensing the vapor in a condenser to give a condensate, and circulating a part of the condensate as reflux liquid into the distillation column from a top side of the distillation column, wherein a phenol-based polymerization inhibitor is added to said condensate and at least one polymerization inhibitor selected from the group consisting of N-oxyl-based polymerization inhibitor, amine-containing polymerization inhibitor and metallic polymerization inhibitor is added to said reflux liquid.

2. The method for distilling (meth)acrylic acid and/or the ester thereof according to claim 1, wherein a part of said reflux liquid is circulated into said distillation column from the top side of the distillation column, and another part of said reflux liquid is circulated into said distillation column from a position lower than the top side of the distillation column and a polymerization inhibitor is added to said reflux liquid circulated into the column from the lower position thereof.

3. The method for distilling (meth)acrylic acid and/or the ester according to claim 2, wherein said polymerization inhibitor added to the reflux liquid being supplied into the distillation column from a position lower than the top side of the distillation column is different from the polymerization inhibitor added to said reflux liquid circulated from the top side of the distillation column.

4. The method for distilling (meth)acrylic acid and/or the ester according to claim 1, wherein said distillation column is a rectification column for producing the final purified product.

5. The method for distilling (meth)acrylic acid and/or the ester according to claim 2, wherein said distillation column is a rectification column for producing the final purified product.

6. The method for distilling (meth)acrylic acid and/or the ester according to claim 3, wherein said distillation column is a rectification column for producing the final purified product.

7. A method for distilling (meth)acrylic acid and/or the ester thereof by withdrawing the vapor generated in a distillation column by distillation from the top of the column, condensing the vapor in a condenser to give a condensate, circulating a part of the condensate thus condensed as reflux liquid into the distillation column from a top side of the distillation column, and feeding another part of said condensate as circulating liquid into said condenser and/or a line connecting said distillation column to said condenser, wherein a phenol-based polymerization inhibitor is added to said condensate and/or said circulating liquid and at least one polymerization inhibitor selected from the group consisting of N-oxyl-based polymerization inhibitor, amine-containing polymerization inhibitor and metallic polymerization inhibitor is added to said reflux liquid.

8. The method for distilling (meth)acrylic acid and/or the ester thereof according to claim 7, wherein a part of said reflux liquid is circulated into said distillation column from the top side thereof, and another part of said reflux liquid is circulated into said distillation column from a position lower than the top side thereof and a polymerization inhibitor is added to said reflux liquid circulated into the column from the lower position thereof.

9. The method for distilling (meth)acrylic acid and/or the ester according to claim 8, wherein said polymerization inhibitor added to the reflux liquid being supplied into the distillation column from a position lower than the top side thereof is different from the polymerization inhibitor added to said reflux liquid circulated from the top side of the distillation column, said condensate, or said circulating liquid.

10. The method for distilling (meth)acrylic acid and/or the ester according to claim 7, wherein said distillation column is a rectification column for producing the final purified product.

11. The method for distilling (meth)acrylic acid and/or the ester according to claim 8, wherein said distillation column is a rectification column for producing the final purified product.

12. The method for distilling (meth)acrylic acid and/or the ester according to claim 9, wherein said distillation column is a rectification column for producing the final purified product.

13. A method for distilling (meth)acrylic acid and/or the ester thereof by withdrawing the vapor generated in a distillation column by distillation from the top of the column, condensing the vapor in a condenser to give a condensate, circulating a part of the condensate as reflux liquid into the distillation column from a top side of the distillation column, and feeding another part of said condensate as circulating liquid into said condenser and/or a line connecting said distillation column to said condenser, wherein a polymerization inhibitor is added to said reflux liquid, a polymerization inhibitor is added to said condensate and/or said circulating liquid, and said polymerization inhibitors are identical to each other, and an amount of the polymerization inhibitor added to said condensate and/or said circulating liquid is 10 to 200 ppm with respect to the (meth)acrylic acid or the ester thereof in the condensate, and an amount of the polymerization inhibitor added to said reflux liquid is 100 to 5000 ppm with respect to the (meth)acrylic acid or the ester thereof in the distillation column, and a concentration of the polymerization inhibitor of said reflux liquid is larger than that of said condensate and/or said circulating liquid.

14. The method for distilling (meth)acrylic acid and/or the ester thereof according to claim 13, wherein said polymerization inhibitor is a phenol-based polymerization inhibitor.

* * * * *